US00PP25189P3

(12) United States Plant Patent
Adams

(10) Patent No.: US PP25,189 P3
(45) Date of Patent: Dec. 30, 2014

(54) APPLE TREE NAMED 'REGAL 13-82'

(50) Latin Name: ***Malus domestica* Bork**
Varietal Denomination: Regal 13-82

(71) Applicant: Kenneth P. Adams, Ephrata, WA (US)

(72) Inventor: Kenneth P. Adams, Ephrata, WA (US)

(73) Assignee: Regal Fruit International, LLC, Ephrata, WA (US)

( * ) Notice: Subject to any disclaimer, the term of this patent is extended or adjusted under 35 U.S.C. 154(b) by 105 days.

(21) Appl. No.: 13/815,581

(22) Filed: Mar. 6, 2013

(65) Prior Publication Data

US 2014/0259237 P1 Sep. 11, 2014

(51) Int. Cl.
*A01H 5/00* (2006.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Paine Hamblen, LLP

(57) ABSTRACT

A new and distinct variety of apple tree as described and which is characterized as to novelty by producing an attractively colored apple which is mature for harvesting and shipment during the first week of October under the ecological conditions prevailing in Central Washington State.

5 Drawing Sheets

Latin name: '*Malus domestica* Bork'.
Varietal denomination: 'REGAL 13-82'.

BACKGROUND OF THE NEW VARIETY

The present invention relates to a new and distinct variety of apple tree '*Malus domestica* Bork' and which has been denominated varietally, hereinafter, as 'REGAL 13-82', and more particularly to an apple tree which bears an attractively colored fruit which is distinguished as to novelty by its firm, yet melting texture, noticeable, apple-like flavor, and its exceptional storage characteristics which makes it ideal for long distance shipping. Additionally, the fruit produced by the present apple tree does not exhibit the physiological disorders of Bitterpit and Lenticel Breakdown that is commonly experienced by the parent trees from which it was derived.

ORIGIN AND ASEXUAL REPRODUCTION

It has long been recognized that an important factor contributing to the success of any new variety of apple tree bearing fruit for the fresh market is its ability to be held for significant periods of time in cold storage with no deleterious affects being noted. Additionally, it is important for new varieties to bear fruit in seasons somewhat different than that of other varieties which it is most closely similar to, so it may command a higher sales price in the marketplace.

The new apple tree variety 'Regal 13-82' is noteworthy in producing fruit which, on the one hand, is ripe for harvesting approximately mid-season, that being the first week of October under the ecological conditions prevailing in Grant County, Washington. Further and in contrast to the apple trees that is mostly closely similar to, that being, its parents the 'Braeburn' apple tree (unpatented); and the 'Honeycrisp' apple tree, U.S. Plant Pat. No. 7,197, the present variety is readily distinguishable in view of its noteworthy cold storage characteristics, and its harvesting date. The new variety is also noteworthy from the standpoint that it resists browning following exposure to the ambient atmosphere, and further has a taste similar to the fruit produced by the 'Honeycrisp' apple tree, but which is available for harvesting in shipment several weeks after the harvesting date of the 'Honeycrisp' apple tree at the same geographical location.

The new variety of apple tree as described, herein, was discovered as a seedling in 2004 following the cross of a 'Braeburn' apple tree, unpatented (Female), and that of a 'Honeycrisp' apple tree (U.S. Plant Pat. No. 7,197) (Male) and which cross was conducted at our test orchard which is located in Grant County, Washington. Fruit from the seedlings produced by this cross were observed in 2007, and the 'Regal 13-82' seedling was selected at that time for further asexual reproduction and evaluation. Second generation trees were then established by removing buds from the selected seedling 'Regal 13-82' and then budding them into M-26 root stock (unpatented), and which were then growing in our same experimental orchard which is located in Grant County, Washington. Subsequently, fruit from the second generation trees were observed in 2011, and then compared and contrasted against fruit produced from the original seedling. The fruit and tree characteristics were established in all respects, and it has been determined that the second generation trees were identical to that originally observed in 2004.

SUMMARY OF THE NEW VARIETY

The 'Regal 13-82' apple tree is characterized principally as to novelty by producing an attractively colored fruit which is ripe for harvesting and shipment approximately mid-season, that being the first week of October under the ecological conditions prevailing in Central Washington state. In contrast to the 'Honeycrisp' apple tree (U.S. Plant Pat. No. 7,197) which matures on or about September 17 under the ecological conditions prevailing in Central Washington, the present new variety is ripe for harvesting and shipment some two and a half weeks later, that is about the first week of October in Central Washington. In 2012, the fruit of the 'Honeycrisp' apple tree were ready for harvesting and shipment about Sep. 17, 2012 in Grant County, Washington, in contrast to the fruit produced by the 'Regal 13-82' apple tree which were harvested on Oct. 5, 2012. In contrast to the other parent of the 'Regal 13-82', that being the 'Braeburn' apple trees growing at the same location, these trees were harvested at approximately the same date. However, the 'Regal 13-82' apple tree, and the fruit produced thereby are clearly distinguishable by their soluble solids content, exterior coloration, and overall shape from each of the parent trees. These and the other distinguishing characteristics as described, hereinafter, make the present apple tree variety highly desirable as a producer of fresh fruit for both local and long distance markets.

Figure 1:
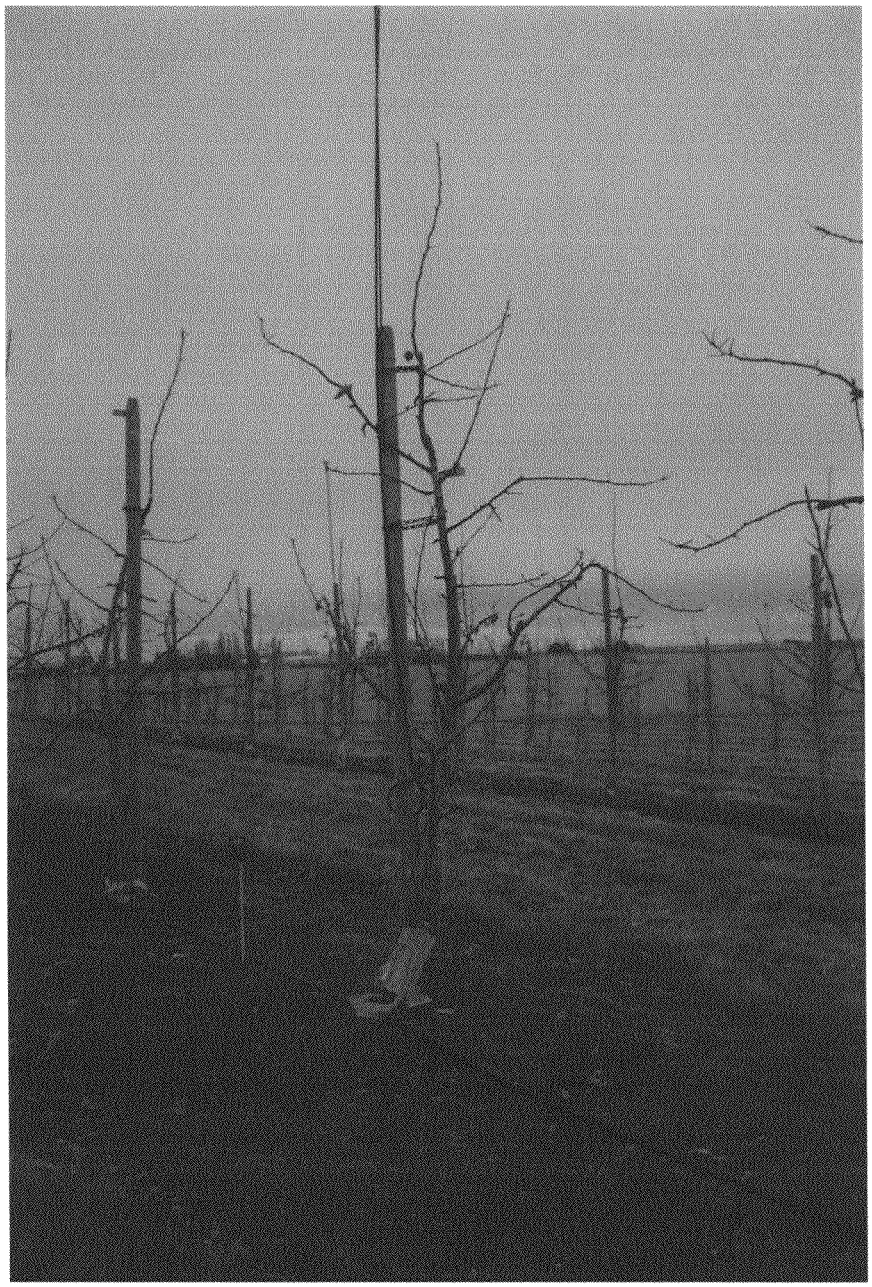
FIG. 1 depicts a dormant, 4 year old, second generation tree of the present variety as seen growing in Grant County, Washington.
Figure 2:
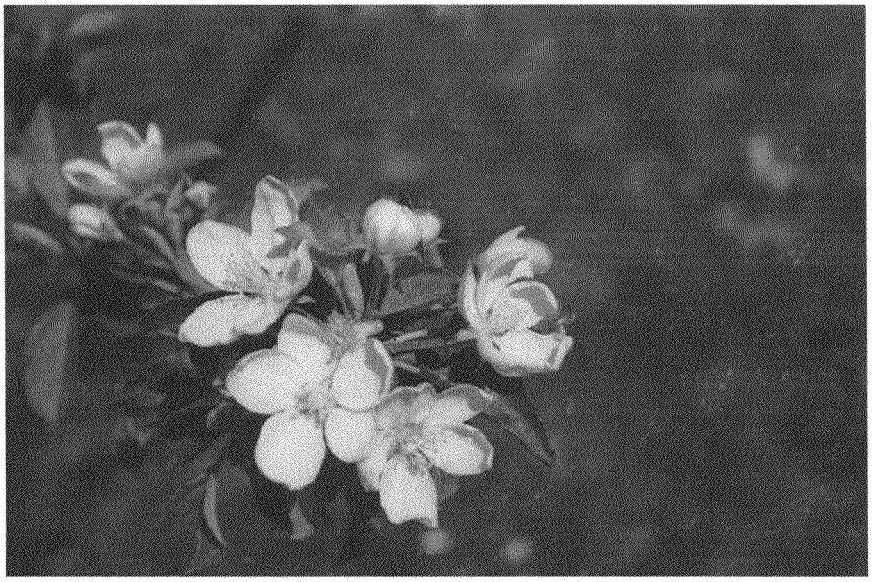
FIG. 2 depicts the blooming characteristics of the flowers found on a 4 year old, second generation tree, of the present variety, as growing in Grant County, Washington.
Figure 3:
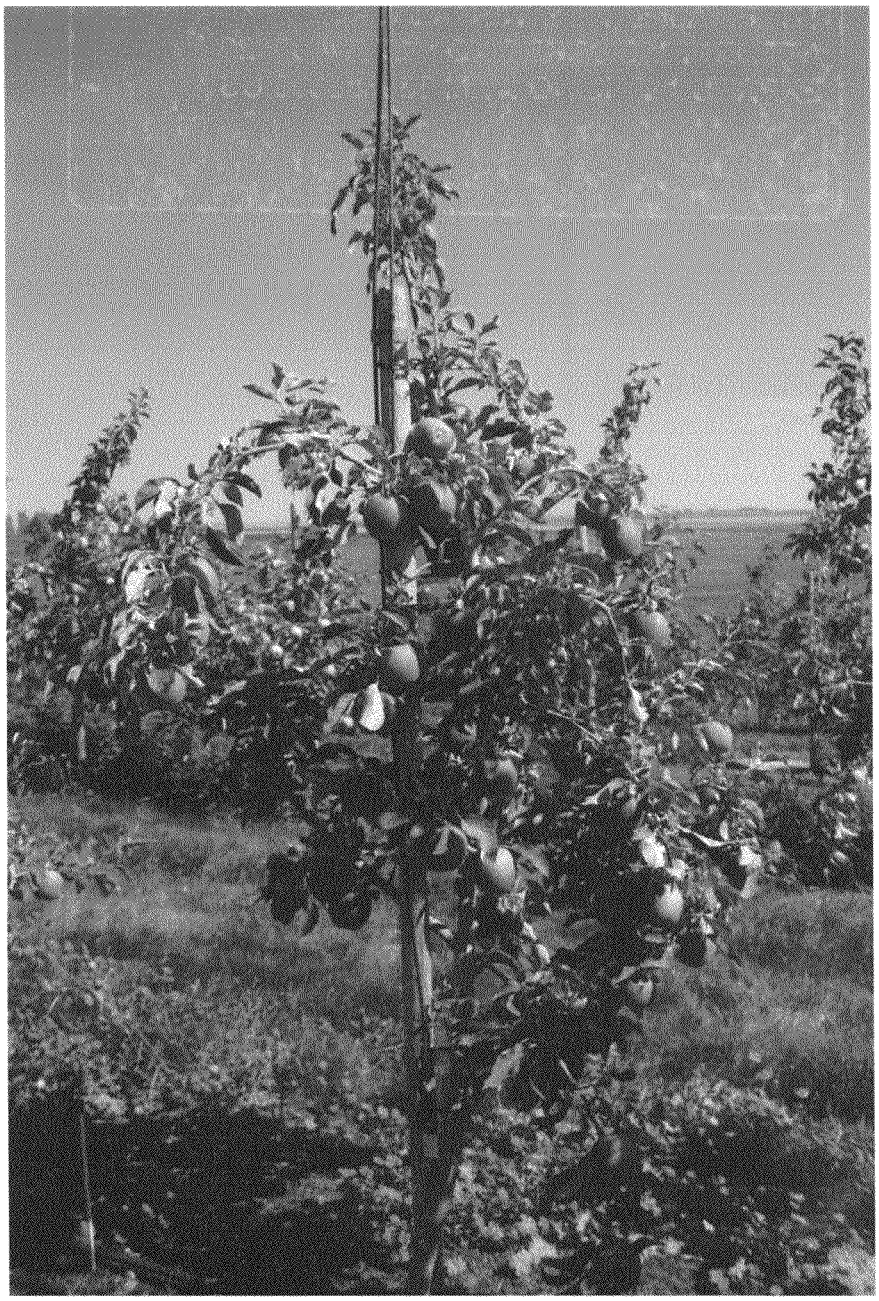
FIG. 3 depicts the growth characteristics of a 4 year old, second generation tree, of the present variety, at full harvest maturity.
Figure 4:
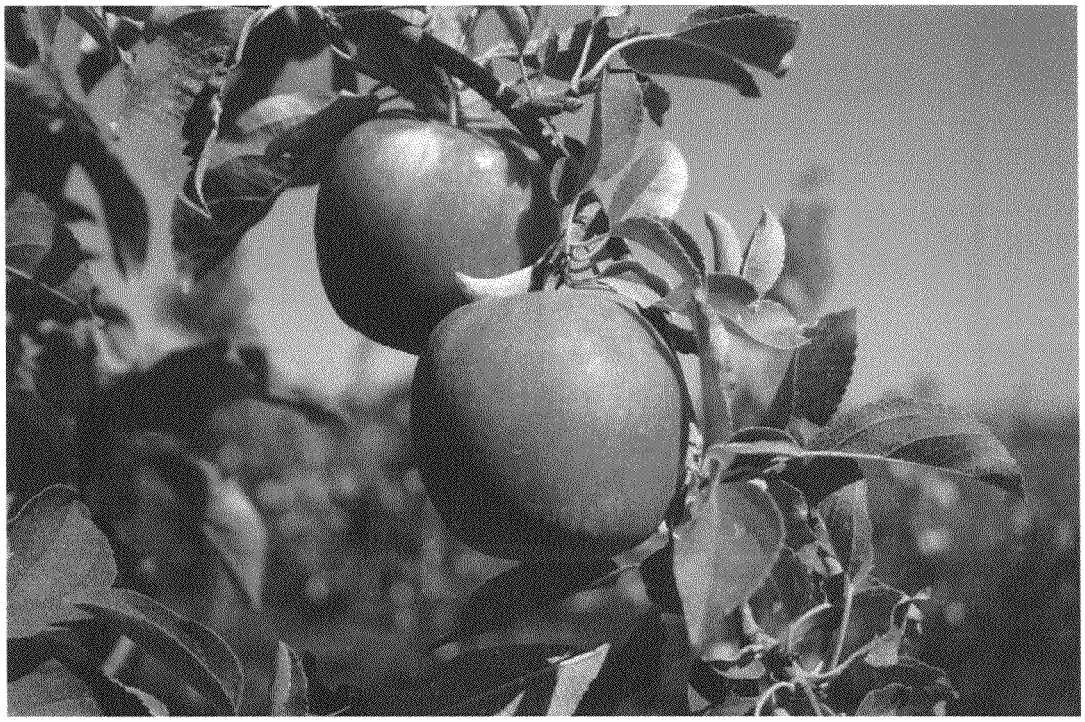
FIG. 4 is a depiction of a fruiting branch of the new variety, at full harvest maturity.
Figure 5:
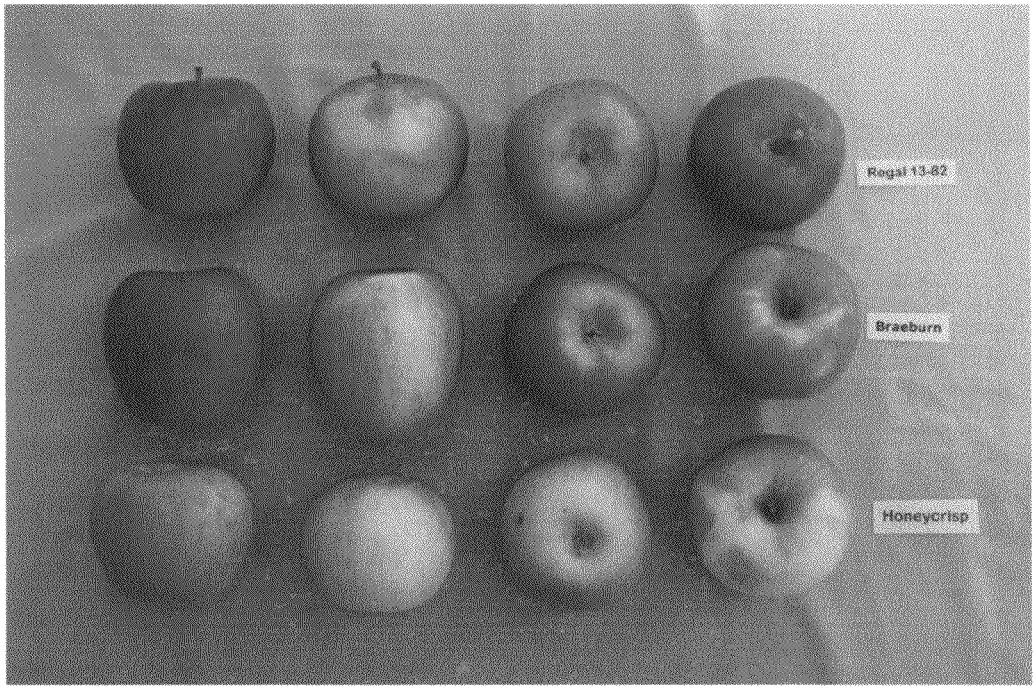
FIG. 5 is a photograph depicting the fruit produced by the present new variety of apple tree as compared to the fruit produced by the 'Braeburn' (unpatented) apple tree and the 'Honeycrisp' apple tree (U.S. Plant Pat. No. 7,197) when grown under the ecological conditions prevailing in Grant County, Washington.

The colors as seen on the enclosed photographs are as nearly true as is reasonably possible in colored photographs of this type. However, due to chemical development, processing and printing, the various colors depicted in these photographs may or may not be accurate when compared to the actual botanical specimens. For this reason, future color references should be made to the color plates provided in The Royal Horticultural Society Colour Chart 2001 and other descriptions provided hereinafter. Occasionally, common color names will also be used.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display the botanical, pomological or other characteristics as set forth, hereinafter. Therefore, this disclosure may not be relied upon to support any future legal claims, including, without limitation, any claims relating to the breach of warranty of merchantability, or fitness for any particular purpose, or non-infringement, which is directed, in whole, or in part, to the present variety.

DETAILED DESCRIPTION

Tree:

*Tree form.*—Generally. — The present variety of apple tree is trained in a central leader-type arrangement. The present variety is also considered to be a consistent bearer and displays moderately heavy spur development.

*Vigor.*—Considered moderately vigorous.

*Overall tree shape.*—Upright and upright spreading as trained to a slender spindle.

*Tree height.*—As trained, about 9 feet.

*Tree width.*—As trained, about 3.75 feet.

*Hardiness.*—The present variety is considered hardy where it is presently grown in Grant County, Washington which is within USDA Hardiness Zone 6(b).

*Fruit productivity.*—Considered moderately heavy for the species.

Trunk:

*Size.*—Generally speaking, the diameter of the trunk when measured at a height of about 20 cm above the graft union is 4.3 cm.

*Trunk bark texture.*—Glabrous.

*Trunk bark color.*—Gray-orange, [RHS 172B].

*Trunk lenticels.*—Generally speaking the lenticels which are present are moderate in number, and average about 15 per 9 square centimeters of surface area. The average width of the respective lenticels is 2.4 mm. The average length of the lenticels is about 5 mm.

*Trunk lenticels.*—Color — Gray-orange (RHS 172 A).

Branches:

*First year branches.*—Diameter — When measured at the midpoint of growth, the branch diameters are about 5.7 mm.

*First year branches.*—Length — On average about 44.3 cm.

*First year branches.*—Color — Gray-orange, (RHS 177A).

*First year branches.*—Lenticels — Generally speaking, the lenticels are numerous and average about 20 per running centimeter of growth.

*Lenticels.*—Shape — Oval, and having a size range of about 0.3 to 0.5 mm in width, and about 1.0 to about 1.3 mm in length.

*Lenticels.*—Color — White (RHS 155 D).

*First year branches.*—Pubescence — As a general matter the pubescence is moderate in density, and covers about 30% to about 50% of the surface area.

*Pubescence color.*—White, (RHS 155 D).

*First year branches.*—Internodes — The internodes distance ranges from about 26.9 mm to about 40.7 mm.

Two year old fruiting branches:

*Diameter.*—When measured at the midpoint of growth, is about 9.2 mm.

*Two year old fruiting branches.*—Spur Development — Generally considered moderate. The spurs range in length from about 15.9 mm to about 20.1 mm in length. Occasionally the spurs are tip bearer.

*Two year old fruiting branches.*—Lenticels — Generally speaking the lenticels are numerous, and average about 12 per square cm of surface area. The Lenticels are round, and are further about 1 to about 2.7 mm in diameter.

*Two year old fruiting branches.*—Buds — As a general matter the buds have a length of about 7.9 mm to about 10 mm.

*Bud diameter.*—About 3.6 mm to about 5.3 mm.

*Bud scale color.*—Red-purple (RHS 59 A). The buds have tip highlights which are gray-purple (RHS 187 A).

*Scaffold branches.*—Size — About 8.6 mm to about 12.9 mm in diameter when measured at a distance of about 5 cm from the trunk.

*Scaffold branches.*—Crotch Angle — As presently trained on the central leader system, the scaffold branches are moderate to flat, that being in a range of about 60° to about 90° from the vertical plane.

*Scaffold branches.*—Color — Gray-orange (RHS 165 A).

*Scaffold branches.*—Lenticels — Generally speaking the lenticels are numerous in number, and average about 8 per square cm of surface area.

*Lenticels.*—Shape — Elongated, and small, and averaging about 1.1 mm in width, and about 1.4 mm in length.

*Lenticels.*—Color — Yellow-white (RHS 158 A).

Leaves:

*Leaf shape.*—Considered broadly acute.

*Leaf texture.*—Dorsal surface — Considered leathery, and the veins appear slightly sunken.

*Leaf texture.*—Ventral Surface — Glabrous and the veins of the leaf protrude outwardly therefrom.

*Leaf sheen.*—A high sheen appears on the dorsal surface of the leaf.

*Leaf pubescence.*—Pubescence appears on the ventral surface only. When it does appear it is fine, and moderate in density, and covers nearly 100% of the surface area.

*Leaf pubescence.*—Color — White (RHS 155 C).

*Leaf length.*—The blade length ranges from about 9.7 cm to about 12 cm.

*Leaf width.*—This characteristic of the leaf is about 5.1 cm to about 7.8 cm.

*Leaf marginal edge.*—Considered serrate.

*Leaf tip.*—Shape — Considered more mucronate than acuminate.

*Leaf base.*—Shape — Considered rounded.

*Leaf stipules.*—None are evident.

*Leaf color.*—Dorsal surface — green (RHS 139 A).

*Leaf color.*—Ventral surface — yellow-green (RHS 147 B).

*Leaf mid-vein.*—Generally speaking, the leaf mid-vein is prominent, and there is a considerable amount of downiness over the entire surface.

*Mid-vein color.*—Ventral surface — Yellow-green (RHS 145 C).

*Mid-vein width.*—When measured at mid-blade it was about 1.6 mm.

*Mid-vein pubescence.*—Color — white (RHS N 155 C).

*Leaf petiole.*—Length — About 3.5 to 4.5 cm. A shallow groove is present along the entire length of the petiole.

*Petiole.*—Diameter — About 1.7 to about 2.3 mm.

*Petiole.*—Color — Dorsal Surface — Yellow-green (RHS 147 C).

*Petiole.*—Color — Ventral Surface — Yellow-green (RHS 145 C).

*Petiole.*—Basal Color — Somewhat highlighted, and appearing orange-red in color (RHS N 34 A).

*Petiole groove.*—Color — Yellow-green (RHS 145 C).

*Petiole pubescence.*—General speaking the pubescence is abundant, and has a moderate density over the entire length, and circumference, of the petiole. The pubescence is white in color (RHS N 155 C).

Flowers: Full bloom was observed on May 4, 2011. The bloom may occur anytime during the first week of May and up to and including May 7 depending upon the ambient weather conditions.

*Number of blossoms per bud.*—About 5 to 6, and typically 6.

*Flower size.*—Considered medium, to medium large for the species. When fully expanded the typical flower is about 45.8 to about 50.8 mm in diameter.

*Flower petal shape.*—Oval with a round base, and a round apex.

*Flower petal width.*—About 16 mm.

*Flower petal length.*—About 22.5 mm.

*Flower petals.*—Color — When unopened, the flower petals have a red-purple color (RHS 59 C).

*Flower petals.*—Color — Opened — When opened, the flower petal is white (RHS N 155 B).

*Flower stamens.*—Numbers — Typically 19 to 20.

*Filament.*—Length — About 4.6 to about 9.4 mm.

*Filament.*—Color — Yellow-green (RHS 145 D).

*Anthers.*—Shape — Heart-like, and having an average width of about 1.5 mm, and an average length of about 1.8 mm.

*Anthers.*—Color — When mature, the anthers have a gray-yellow color (RHS 161 B).

*Pistil.*—Length — About 11.1 mm to about 13.3 mm.

*Styles.*—Number — Typically five, and fused near the base. A white pubescence is found at the union. This color is not distinctive of the variety.

*Average pistil length.*—About 12.3 mm.

*Pistil color.*—Yellow-green (RHS 145 C).

*Stigma.*—Shape — Club like.

*Stigma.*—Color — Gray-yellow (RHS 162 A).

*Pollen abundance.*—Considered abundant.

*Mature pollen color.*—Gray-yellow (RHS 162 A).

*Sepals.*—Numbers — Five per blossom are typically found, and they are usually curled backwards towards the peduncle.

*Sepals.*—Shape — Considered thin, and lanceolate, with the tip being acuminate, and the base be truncate in shape.

*Sepals.*—Length — About 7.4 mm.

*Sepals.*—Width — About 4 mm.

*Sepals.*—Color — Abundant white pubescence is present on both the dorsal and ventral surfaces. The sepal color is green in color (RHS 143 C). The sepal tips are highlighted with a gray-orange color (RHS 173 A).

*Peduncle.*—Length — About 25.5 to about 27.1 mm.

*Peduncle.*—Diameter — About 1.2 to about 1.4 mm.

*Peduncle.*—Color — Green (RHS 143 C).

*Peduncle.*—Surface Texture — A considerable amount of white downiness is present over the entire surface area. This color is not distinctive of the variety, however.

Fruit:

*Maturity when described.*—The present fruit is described at full commercial maturity. The following measurements were taken from second generation trees presently growing in a test orchard which is located in Grant County, Washington.

*Fruit form.*—Considered oblate, round, and conical. The Equatorial Diameter cross-section is considered regular.

*Fruit size.*—Considered medium to medium large for the species with at normal crop loading levels.

*Equatorial diameter.*—About 8.2 cm.

*Axial diameter.*—About 7.3 cm.

*Stem.*—Length — Considered long, about 2.3 cm to about 3.7 cm.

*Stem.*—Diameter — About 2.2 mm to about 2.7 mm.

*Stem.*—Cavity — Average width — 3.7 cm.

*Stem cavity.*—Average depth — about 2.1 cm.

*Stem cavity.*—Shape — Acute and russet free.

*Stem cavity.*—Lipping — None is apparent.

*Basin cavity.*—Width — About 3.2 cm.

*Basin cavity.*—Depth — About 1.0 cm.

*Basin cavity.*—Shape — Rounded and lightly crowned around the eye. The base has a downy appearance.

*Eye.*—Erect and convergent. A light white downiness appears at the base.

*Sepal color.*—Yellow-green (RHS 151 D).

*Fruit skin appearance.*—Generally speaking, the fruit skin appears more streaked than mottled, and is glossy and slightly rugose. The bloom appearing on the fruit skin is moderate in intensity.

*Fruit skin.*—Thickness — Considered thin.

*Fruit skin.*—Texture — Considered somewhat brittle, and on the tender side.

*Fruit skin.*—Color — The over color of the fruit skin is red (RHS 53 A). The under color of the fruit skin is red (RHS 53 B).

*Fruit skin.*—Lenticels — Present, distinct, and substantially evenly distributed. The lenticels number about 10 per square cm of surface area.

*Lenticels.*—Shape — Round and about 0.1 to 0.2 mm in diameter.

*Lenticels.*—Color — White. This color is not distinctive of the variety, however.

*Fruit core.*—Position — Sessile.

*Fruit core.*—Line Position — Basal, and clasping.

*Fruit cell.*—Tufting — Present, but considered light, and irregular.

*Fruit cell shape.*—Generally — Ovate.

*Tube.*—Shape — Cone-like.

*Stamen position.*—Generally speaking, median.

*Axis.*—Considered axial and closed.

*Seed number.*—Variable, from 1 to 3, and typically 2.

*Seed shape.*—Mostly acuminate, however some acute shapes may be found.

*Seed length.*—About 9.8 mm.

*Seed width.*—about 4.5 mm.

*Seed color.*—Gray-orange (RHS 166 A).

*Flesh.*—Generally — It is considered very firm, very crisp and snappy, and further is considered very juicy, and has a melting texture and a sub-acid flavor.

*Flesh.*—Color — Yellow (RHS 4 D).

*Flesh.*—Aroma — Mild, and apple-like.

*Date of harvest maturity.*—In 2012, Oct. 5 under the conditions prevailing in Grant County, Washington. Tree Productivity: Not distinctive of the present variety. In view of the many variables which effect tree productivity including horticulural practices; irrigation; fertilization; pest control and crop density, this value can be quite variable. Based upon the present crop density, at harvest, the new variety produces about 22 bins of apples per acre. A full apple bin is about 800 lbs.

*Keeping quality.*—Considered excellent. The variety has been kept up to six months in common storage with no deleterious affects noted. The flesh of the present fruit resists browning after being exposed to the ambient atmosphere.

*Fruit pressure.*—Generally — At harvest maturity the new variety typically has a fruit pressure of about 19.8. In contrast, the fruit produced by the 'Braeburn' apple tree typically has a fruit pressure of 20.3 lbs, and the 'Honeycrisp' apple tree produces a fruit having a fruit pressure of about 16.5 lbs, at harvest.

*Brix.*—At full harvest maturity, the new variety has a brix of about 13.4° as compared to the fruit produced by the 'Braeburn' apple tree (unpatented) and which is typically about 11.2° when grown under typical cultural conditions. Still further the fruit produced by the 'Honeycrisp' apple tree, at full harvest maturity produces a fruit having a brix of about 14.8°.

*pH.*—At full harvest maturity the new, novel variety of apple tree as described herein produces fruit having a pH, upon harvesting, of about 3.53. In contrast, the fruit produced by the 'Braeburn' apple tree at full harvest maturity has a pH of about 3.34. Still further to the fruit produced by the 'Honeycrisp' apple tree (U.S. Plant Pat. No. 7,197) typically has a pH of about 3.38 at harvest.

*Acid.*—At full harvest maturity the fruit of the new variety of apple tree typically has an acid content of about 5 grams per liter. This is in contrast to the parents of the present variety, that being the 'Braeburn' apple tree (unpatented) which at harvest maturity produces fruit having an acid content of about 6.72 grams per liter, and the fruit produced by the 'Honeycrisp' apple tree which at full harvest maturity produces has an acid level of about 4.5 grams per liter. After 3 months in common storage, the present new variety of apple tree has fruit which displays a fruit pressure of about 19.2 lbs; a Brix of 13.6°, a pH of 3.56 and an acid content of about 5.07 grams per liter.

*Pollination.*—Any diploid apple that blooms in approximately the same season may be used for pollination purposes.

*Fruit use.*—Fresh dessert. The present fruit has excellent eating qualities that is considered snappy, juicy, sweet and with excellent acid balance and which further has a melting skin.

*Disease and insect resistance.*—The present variety is considered to be susceptible to all insects and diseases found in the region of Central Washington. The fruit of the present variety does not exhibit any physiological disorders on the tree nor during storage for the duration of normal storage lengths as recited in this application.

Although the new variety of apple tree herein described possesses the characteristics when grown under the ecological conditions prevailing in Grant County, Washington, it is to be understood that variations of the usual magnitude and characteristics incident to changes in growing conditions, fertilization, pruning and pest control are to be expected.

Having thus described and illustrated my new variety of apple tree, what I claim is new and desire to secure by plant Letters Patent is:

1. A new and distinct variety of apple tree, substantially as illustrated and described, and which is characterized principally as to novelty by producing an attractively colored apple which is mature for harvesting and shipment during the first week in October under the ecological conditions prevailing in Grant County, Washington.

* * * * *